United States Patent [19]

Thominet

[11] 3,995,036

[45] Nov. 30, 1976

[54] METHODS OF TREATING A MAMMAL AFFLICTED WITH EXCESSIVE HISTAMINE WITH DIALKYLAMINOALKYL ETHERS OF 2-ALKOXY-3,5-DIHALOBENZENE AND SALTS THEREOF

[75] Inventor: Michel Léon Thominet, Paris, France

[73] Assignee: Societe d'Etudes Scientifiques et Industrielles de l'Ile-de-France, Paris, France

[22] Filed: Apr. 26, 1976

[21] Appl. No.: 680,128

Related U.S. Application Data

[60] Division of Ser. No. 577,098, May 13, 1975, which is a division of Ser. No. 369,567, June 13, 1973, Pat. No. 3,904,622, which is a continuation-in-part of Ser. No. 80,211, Oct. 12, 1970, abandoned, which is a continuation-in-part of Ser. No. 798,164, Feb. 10, 1969, abandoned.

[30] Foreign Application Priority Data

Feb. 16, 1968 France .......................... 68.140294
May 10, 1968 France .......................... 68.151632

[52] U.S. Cl. ............................ 424/248; 424/325
[51] Int. Cl.² ................ A61K 31/13; A61K 31/535
[58] Field of Search ........................... 424/248, 325

[56] References Cited

UNITED STATES PATENTS

| | | | |
|---|---|---|---|
| 2,967,201 | 1/1961 | Soper .............................. | 260/570.7 |
| 3,235,597 | 2/1966 | Mills et al. ...................... | 260/570.5 |

Primary Examiner—Stanley J. Friedman
Attorney, Agent, or Firm—Frank M. Nolan

[57] ABSTRACT

Excessive histamine in mammals is effectively relieved by the administration of dialkylaminoalkyl ethers of 2-alkoxy-3,5-dihalobenzenes. The compounds are relatively non-toxic in dosages required to alleviate such condition.

7 Claims, No Drawings

METHODS OF TREATING A MAMMAL AFFLICTED WITH EXCESSIVE HISTAMINE WITH DIALKYLAMINOALKYL ETHERS OF 2-ALKOXY-3,5-DIHALOBENZENE AND SALTS THEREOF

This application is a division of the copending application Ser. No. 577,098, filed May 13, 1975. The application Ser. No. 577,098 is a division of the application Ser. No. 369,567, filed June 13, 1973, now U.S. Pat. No. 3,904,622. The application Ser. No. 369,567 is a continuation-in-part of the copending U.S. Pat. application of M. L. Thominet, Ser. No. 80,211, filed Oct. 12, 1970, now abandoned. The application Ser. No. 80,211 is a continuation-in-part of the U.S. Pat. application Ser. No. 798,164, filed Feb. 10, 1969, now abandoned.

This invention relates to dialkylaminoalkyl ethers of 2-alkoxy-3,5-dihalobenzene, their non-toxic acid addition salts with a mineral or organic acid, their non-toxic quaternary ammonium salts and the process of producing these compounds. These compounds have significant pharmacological properties, particularly as spasmogenic agents and are adapted for the treatment of mammals with them.

The dialkylaminoalkyl ethers of the invention have the formula:

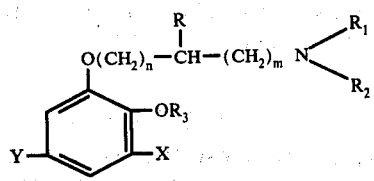

in which $m$ is an integer from 0 through 2 and $n$ is an integer from 0 through 2; R and $R_3$ are hydrogen or lower alkyl of less than 6 carbon atoms; $R_1$ and $R_2$ are hydrogenm lower of alkyl of less than 6 carbon atoms or form a five or six membered heterocyclic radical; and X and Y are halogens.

Examples of lower alkyl having less than 6 carbon atoms are methyl, ethyl, propyl, isobutyl and amyl. Examples of five or six membered heterocyclic radicals are pyrrolidyl, piperidyl, morpholyl, piperazinyl, n-alkylpiperidyl and imidazolyl. The halogens X and Y may be the same or different; for example, they may be fluorine, chlorine or bromine.

The acid addition salts of the dialkylaminoalkyl ethers of 2-alkoxy-3,5-dihalobenzene are those produced by reacting the base with a mineral or organic acid such as hydrochloric acid, hydrobromic acid, hydroiodic acid, phosphoric acid, sulfuric acid, citric acid, tartaric acid, or ethane sulfonic acid. The quaternary ammonium salts may be obtained by reacting the benzamide with an aliphatic or aromatic alkylating agent, such as methyl chloride, methyl bromide, methyl iodide, dimethyl sulfate, methyl benzene sulfonate, methyl p-toluene sulfonate, ethyl bromide, propyl bromide or benzyl chloride.

The dialkylaminoalkyl ethers of 2-alkoxy-3,5-dihalobenzene amides of this invention are produced by acetylating a monoether of pyrocatechol, then halogenating the compound obtained, then deacetylating the compound and treating it with an alkylaminoalkyl chloride.

A more comprehensive understanding of this invention is obtained by reference to the following examples:

EXAMPLE I

(2'-DIETHYLAMINOETHOXY-2-METHOXY-3,5-DICHLOROBENZENE HYDROCHLORIDE

STAGE A: 3,5-dichloroguaiacol 62 g of guaiacol (0.5 mole) is acetylated in a 250 ml balloon flask provided with a reflux condenser by means of acetic anhydride, in the presence of a few drops of concentrated sulfuric acid. When the reaction is concluded, the sulfuric acid is neutralized with sodium acetate and then, when the solution has been cooled, the guaiacol acetate is chlorinated.

The above solution is placed in a one liter balloon flask provided with an agitator and a thermometer. 150 ml of acetic acid is then added. 160 g of chlorosuccinimide is then added in small quantities. The suspension is then heated to from 50° to 55° C and is then kept in an oven at 55° C for 117 hours.

When the reaction is complete, cooling is effected and two liters of water is added with agitation being maintained. The chlorinated derivative crystallizes. It is dried without heating, washed and deacetylated by means of 125 ml of 30% soda lye. The product is distilled and then recrystallized from petroleum ether. 66 g of 3,5-dichloroguaiacol is obtained (melting point: 62° to 62° C) (yield 68%)

STAGE B: (2'-diethylaminoethoxy)-2-methoxy-3,5-dichlorobenzene 50 g of 3,5-dichloroguaiacol (0.25 mole) is poured into a solution of sodium ethylate prepared from 6 g of sodium in 78 ml. of absolute alcohol.

39 g (0.26 mole + 10% excess) of 1-diethylamino-2-chloroethane is added to the red solution obtained.

Upon gentle heating, the solution becomes cloudy. Sodium chloride precipitates. Heating under reflux is then applied for 7 hours. Cooling is effected and then 300 ml of water and 25 ml of concentrated hydrochloric acid are added. The aqueous solution is filtered, treated with black and the base is precipitated by 40 ml of ammonia and extracted with ether. After distillation of the ether, 51 g (yield: 72%) of (2'-diethylaminoethoxy)-2-methoxy-3,5-dichlorobenzene is obtained (boiling point/7 mm: 165° to 166° C).

STAGE C: (2'-diethylaminoethoxy)-2-methoxy-3,5-dichlorobenzene hydrochloride

The base prepared above is dissolved in 100 ml of acetone and 6 g 35% dry hydrochloric acid in 20 ml of acetone is added. (2'-diethylaminoethoxy)-2-methoxy-3,5-dichlorobenzene hydrochloride precipitates, which is then dried without heating, washed with acetacetone and then dried. 51 g of the product is obtained (melting point: 132° to 134° C).

ANALYSIS Calculated %: C: 47.49, H: 6.09, Cl: 32.42, N: 4.26; Actual %: C: 47.31, H: 6.14, Cl: 32.24, N: 4.18.

EXAMPLE II

(3'-DIMETHYLAMINOPROPOXY)-2-METHOXY-3,5-DICHLOROBENZENE HYDROCHLORIDE

Stage A is similar to that described in Example I.

STAGE B: (3'-dimethylaminopropoxy)-2-methoxy-3,5-dichlorobenzene 63 g of 3,5-dichloroguaiacol (0.32 mole) is poured into a solution of sodium ethylate obtained from 7.5 g of sodium and 100 ml of ethyl alcohol. 44 g (0.326 mole + 10% excess) of 1-dimethylamino-3-chloropropane is added and the resulting mixture is heated under reflux for 6 hours. Precipitation of sodium chloride is observed. It is cooled and dissolved in 300 ml of water and 30 ml of concentrated hydrochloric acid. The aqueous solution is treated with black. The resulting base is precipitated by adding ammonia. It is extracted with ether, then the ether is removed and the residue is distilled.

63 g (yield 70%) of (3'-dimethylaminopropoxy)-2-methoxy-3,5-dichlorobenzene is obtained (boiling point/ 25 mm: 190 to 195° C).

STAGE C: (3'-dimethylaminopropoxy)-2-methoxy-3,5-dichlorobenzene hydrochloride

The base prepared above is dissolved in 180 ml of acetone. 7.85 g of dry hydrochloric acid dissolved in 70 ml of acetone is added. (3'-dimethylaminopropoxy)-2-methoxy-3,5-dichlorobenzene hydrochloride precipitates. It is a white solid (melting point: 138° to 140° C).

ANALYSIS: Calculated %: C: 45.79, H: 5.72, Cl: 33.86, N: 4.45; Actual %: C: 45.59, H: 5.79, Cl: 33.72, N: 4.30.

EXAMPLE III (3'-DIETHYLAMINOPROPOXY)-2-METHOXY-3,5-DICHLOROBENZENE HYDROCHLORIDE

Stage A is similar to that described in Example I.

STAGE B: (3'-diethylaminopropoxy)-2-methoxy-3,5-dichlorobenzene

The 66 g of 3,5-dichloroguaiacol (0.34 mole) prepared above is added to a solution of sodium ethylate prepared from 7 g of sodium and 130 ml of absolute alcohol. 55 g of diethylamino-3-chloropropane (0.34 mole + 10% excess) is added to the resulting red solution.

Gentle heating is applied; after 5 minutes, the solution becomes cloudy. Sodium chloride precipitates. Heating under reflux is then applied for 2 hours.

Cooling is effected and water is added. The amine precipitates. The mixture is decanted and extracted a number of times with methylene chloride, then the organic solution is washed by means of a 4% sodium solution and then with water. It is dried over potassium carbonate and the solvent is distilled. 96 g of (3'-diethylaminopropoxy)-2-methoxy-3,5-dichlorobenzene is obtained. (yield: 95%)

STAGE C: (3'-diethylaminopropoxy)-2-methoxy-3,5-dichlorobenzene hydrochloride

The base prepared above is dissolved in twice its weight of acetone.

Dry hydrochloric acid is bubbled into the same volume of acetone and this solution is poured into the base until methyl red changes color. The hydrochloride crystallizes. It is dried without heating, washed, dried in the air and then in an oven at 30° C. It is recrystallized a number of times from isopropanol. 51 g of (3'-diethylaminopropoxy)-2-methoxy-3,5-dichlorobenzene hydrochloride is obtained (melting point: 142° C) (yield: 48%).

ANALYSIS: Calculated %: C: 49.05, H: 6.42, Cl: 31.09, N: 4.09; Actual %: C: 49.16, H: 6.46, Cl: 30.90, N: 4.19.

EXAMPLE IV (3'-MORPHOLINOPROPOXY)-2-METHOXY-3,5-DICHLOROBENZENE HYDROCHLORIDE

Stage A is similar to that described in Example I.

STAGE B: (3'-morpholinopropoxy)-2-methoxy-3,5-dichlorobenzene 54 g of 3,5-dichloroguaiacol (0.28 mole) is added to sodium ethylate produced by reacting 6.44 g of sodium on 84 ml of ethyl alcohol. 51 g (0.28 mole + 10% excess) of 1-chloro-3-morpholinopropane is added to the resulting solution. The mixture is heated under reflux for 8 hours. Precipitation of sodium chloride is observed. Cooling is effected and then the mixture is dissolved in 300 ml of water and 30 ml of concentrated hydrochloric acid. The resulting solution is filtered, then ammonia is added to precipitate the base which is extracted with ether. The ether is eliminated and the residue is distilled under vacuum.

73 g (yield: 82%) of (3'-morpholinopropoxy)-2-methoxy-3,5-dichlorobenzene is obtained (boiling point/ 16 mm: 197° to 200° C).

STAGE C: (3'-morpholinopropoxy)-2-methoxy-3,5-dichlorobenzene hydrochloride

The base prepared above is dissolved in 150 ml of acetone. 8.32 g of dry hydrochloric acid dissolved in 50 ml of acetone is added; (3'-morpholinopropoxy)-2-methoxy-3,5-dichlorobenzene hydrochloride precipitates, which is dried without heating, washed on a filter with acetone and dried. (Weight: 73 g) (Yield: 94%) (Melting point: 183° to 184° C).

ANALYSIS: Calculated %: C: 47.12, H: 5.61, Cl: 29.87, N: 3.93; Actual %: C: 47.33, H: 5.72, Cl: 29.77, N: 3.92.

EXAMPLE V (3'DIETHYLAMINOISOPROPOXY)-2-METHOXY-3,5-DICHLOROBENZENE OXALATE

Stage A is similar to that described in Example I.

STAGE B: (3'-diethylaminoisopropoxy)-2-methoxy-3,5-dichlorobenzene 63 g of 3,5-dichloroguaiacol (0.326 mole) is added to sodium ethylate which is prepared by dissolving 7.5 g of sodium in 100 ml of alcohol. There is added to the resulting solution 54 g (0.326 mole + 10% excess) of β-chloropropyl diethylamine. The mixture is heated for 7 hours, sodium chloride precipitates. It is dissolved with 300 ml of water and 4.5 ml of concentrated hydrochloric acid. The solution is filtered and 60 ml of ammonia is added. The precipitated base is extracted with ether. The ether is eliminated and the residue is distilled.

70 g (yield: 7 to 10%) of (3'-diethylaminoisopropoxy)-3,5-dichlorobenzene is obtained (boiling point/ 5 mm: 166° to 167° C).

STAGE C: (3'-diethylaminoisopropoxy)-2-methoxy-3,5-dichlorobenzene oxalate

The base prepared above is dissolved in 130 ml of absolute alcohol; 21 g of oxalic acid which is previously dissolved in 40 ml of alcohol is added. (3'-diethylaminoisopropoxy)-2-methoxy-3,5-dichlorobenzene oxalate precipitates, which is dried without heating, washed with alcohol and dried. (Melting point: 128° C).

ANALYSIS: Calculated %: C: 48.48, H: 5.81, Cl: 17.93, N: 3.53; Actual %: C: 48.28, H: 5.98, Cl: 17.80, N: 3.39.

EXAMPLE VI

(3'-DIETHYLAMINOPROPOXY)-2-METHOXY-3,5-DICHLOROBENZENE BROMOMETHYLATE

The base is prepared as described in Stages A and B of Example III.

A methanolic solution of methyl bromide (18 g of Br CH$_3$ for 161 ml of solution, i.e. 0.17 mole + 10% excess) is poured into 51 g (0.17 mole) of (3'-diethylaminopropoxy)-2-methoxy-3,5-dichlorobenzene dissolved in 100 ml of methanol. The solution is maintained at ambient temperature for about 90 hours. The alcohol is distilled under vacuum until a constant weight is reached. The resulting product is recrystallized from acetone. The crystals are dried without heating, washed with acetone and dried at 55° C. 43 g of white crystals of (3'-diethylaminopropoxy)-2-methoxy-3,5-dichlorobenzene bromomethylate is obtained. This product is very hygroscopic. (Melting point: 114° to 115° C) (Yield: 63%)

ANALYSIS: Calculated %: C: 44.89, H: 5.98, Br: 19.95, Cl: 17.70, N: 3.49; Actual %: C: 44.76, H: 6.10, Br: 20.03, Cl: 17.56, N: 3.28.

The high degrees of toxicity, studied on mice, have shown that the compounds, subject of the present invention, are of a toxicity which is quite compatible with therapeutic use. The following table is given by way of example:

| COMPOUND | D.L. 50 in mg/kg Compound in base form | | | |
|---|---|---|---|---|
| | IV | IP | SC | PO |
| (3'-diethylaminopropoxy)-2-methoxy-3,5-dichlorobenzene | 34.8 31.3 | 181 | 608 | 737 |

1. The spasmogenic action of the compounds of the invention was studied on detached guinea-pig ileum.

Taking a section of detached guinea-pig ileum, the severity of the contractions caused by increasing doses of the product under study, namely 0.1 µg/ml − 0.2 µg/ml − 0.4 µg/ml, is measured.

This study revealed the powerful spasmogenic properties of the medicaments of the invention.

2. The atropine counteracting action was also studied on detached guinea-pig ileum.

A section of ileum is suspended in aerated Tyrode liquid. (3'-diethylsminopropoxy)-2-methoxy-3,5-dichlorobenzene in a concentration of $2.10^{-7}$ (0.2 µg/ml) is left in contact with the muscle for 30 seconds. The resulting contractions are registered and repeated every 6 minutes until the response stabilizes.

Atropine is added to the bath 30 seconds before (3'-diethylaminopropoxy)-2-methoxy-3,5-dichlorobenzene in doses such that inhibition of the contraction of from 20 to 80% is obtained, permitting graphic determination of the counteracting dose 50.

| Spasmogenic Agents | Atropine Mean Counteracting Dose 50 in µg/ml |
|---|---|
| (3'-diethylaminopropoxy)-2-methoxy-3,5-dichlorobenzene Spasmogenic dose: $2.10^{-7}$ | 1.9 (a) |
| Acetylcholine $1.10^{-7}$ | 0.010 (a) |

(a) Determined over 12 tests, each section of ileum being successively subjected to the spasmogenic action of (3'-diethylaminopropoxy)-2-methoxy-3,5-dichlorobenzene, and acetylcholine.

Besides their spasmogenic properties, the medicaments of the invention have various interesting pharmacological properties which are indicated in the following table:

| Method | Animal | Doses mg/kg | Manner of administration | (3'-diethylaminopropoxy)-2-methoxy-3,5-dichlorobenzene |
|---|---|---|---|---|
| Gastro-intestinal passage Measured 40 min. after administration of the product Agent: vegetable charcoal | Mouse | DE 50 | S.C. | nil effect from 0.001 mg/kg to 200 mg/kg |
| Antiemetic activity Measured 30 min. (SC) or 1 hour (oral) after administration of the product. Agent: apomorphine 100 µg/kg SC | Dog | DE 50 | S.C. | 16 % effect with 0.25 mg/kg |
| Cataleptic activity Measured at maximum effect, i.e. from 300 to 360 min. after administration of the product. | Rat | DE 50 | S.C. | 30 % effect with 200 mg/kg |
| Traction method Measured 30 min. after administration of the product. | Mouse | DE 50 | S.C. P.O. | 197 40 % effect with 150 mg/kg |
| Potentialisation of barbituric narcosis Measured 30 min. after administration of the product. Agent: pentobarbital 60 mg/kg IP | Mouse | Index 2 | I.P. P.O. | 55.4 Index : 1.23 with 200 mg/kg |
| Spontaneous motivity Measured 15 min. (I.P.) or 60 min. (P.O.) after administration of the product. | Winter and Flataker test Mouse | DE 50 DE 50 | I.P. P.O. I.P. P.O. | 49.1 effect nil with 200 mg/lg 16.1 − 19.7 105 |
| | Activograph | | | |
| Antimescaline activity Measured 15 min. after administration of the product. Agent: mescaline 50 mg/kg I.M. | Mouse | DE 50 | I.P. | 30 % effect with 100 mg/kg |
| Anti-apomorphine activity (JANSSEN test) | | | | |

-continued

| Method | Animal | Doses mg/kg | Manner of administration | (3'-diethylaminopropoxy)-2-methoxy-3,5-dichlorobenzene |
|---|---|---|---|---|
| Measured 80 min. after administration of the product. Agent: apomorphine 1.25 mg/kg I.V. | Rat | DE 50 | S.C. | 30 % effect with 600 mg/kg |
| Antimorphine activity (STRAUB test) Measured 60 to 120 min. after administration of the product. Agent: morphine 30 mg/kg S.C. | Mouse | DE 50 | P.O. | 313 |
| Antitremorine activity (CHEN method) Measured 60 min. after administration of the product. Agent: tremorine 7.5 mg/kg I.M. | Mouse | DE 50 | I.P. | 94.7 |
| Rotating shaft test Measured from 10 to 30 min. after administration of the product. | Mouse | DE 50 | I.P. P.O. | 71.5 18 % effect with 200 mg/kg |
| Evasion test (KNEIPP method) Measured 1 hour after administration of the product. | Mouse | DE 50 | I.P. | 75.9 |
| Antiserotonine action Reduction with respect to reference hypertension caused by sorotonine; 25 γ/kg I.V. | Dog | DE 50 | I.V. | 19 |
| Anticonvulsant activity — Electrical crisis measured at peak effect | Mouse | DE 50 | S.C. | 37.1 |
| Anticonvulsant activity — Chemical Crisis Measured 30 min. after adminis- Agent: Cardiazol 70 mg/kg I.V. | Mouse | DE 50 | P.O. I.P. | 143 |

| Method | | Animal | Doses mg/kg | Manner of administration | (3′-diethylamino-propoxy)-2-methoxy-3,5-dichlorobenzene |
|---|---|---|---|---|---|
| thetic system | Vagal Excitation % reduction with respect to reference hypotension | Dog | 16 8 4 2 1 | I.V. | R = 51 % R = 21 % R = 11 % R = 0 % R = 0 % |

The experimental results were confirmed in clinics where the products were administered in the form of compressed tablets or phials of a pharmacologically acceptable salt.

What is claimed is:

1. The method of treating a mammal afflicted with excessive histamine which comprises administering to said mammal a therapeutically effective amount of a dialkylaminoalkyl ether of 2-alkoxy-3,5-dihalobenzene, a non-toxic acid addition salt thereof or a quaternary ammonium salt thereof, said dialkylaminoalkyl ether of 2-alkoxy-3,5-dihalobenzene having the formula:

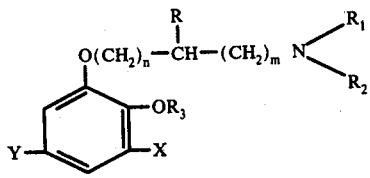

in which $m$ is an integer from 0 through 2; and $n$ is an integer from 0 through 2; R is hydrogen or lower alkyl of less than 6 carbon atoms; $R_3$ is lower alkyl of less than 6 carbon atoms; $R_1$ and $R_2$ are hydrogen, lower alkyl of less than 6 carbon atoms or form, together with the nitrogen atoms, morpholino; and X and Y are the same halogens.

2. The method of claim 1 in which the ether administered is (2′-diethylaminoethoxy)-2-methoxy-3,5-dichlorobenzene hydrochloride.

3. The method of claim 1 in which the ether administered is (3′-dimethylaminopropoxy)-2-methoxy-3,5-dichlorobenzene hydrochloride.

4. The method of claim 1 in which the ether administered is (3′-diethylaminopropoxy)-2-methoxy-3,5-dichlorobenzene hydrochloride.

5. The method of claim 1 in which the ether administered is (3′-morpholinopropoxy)-2-methoxy-3,5-dichlorobenzene hydrochloride.

6. The method of claim 1 in which the ether administered is (2′-diethylamino-1′-methyl-ethoxy)-2-methoxy-3,5-dichlorobenzene oxalate.

7. The method of claim 1 in which the ether administered is (3′-diethylaminopropoxy)-2-methoxy-3,5-dichlorobenzene bromomethylate.

* * * * *